United States Patent
Ding

(10) Patent No.: US 6,299,596 B1
(45) Date of Patent: *Oct. 9, 2001

(54) METHOD OF BONDING POLYMERS AND MEDICAL DEVICES COMPRISING MATERIALS BONDED BY SAID METHOD

(75) Inventor: Ni Ding, Plymouth, MN (US)

(73) Assignee: Schneider (USA) Inc., Plymouth, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/148,389

(22) Filed: Sep. 4, 1998

Related U.S. Application Data

(60) Provisional application No. 60/078,839, filed on Mar. 20, 1998.

(51) Int. Cl.[7] .......................... A61M 29/00; B32B 31/12; B32B 31/28
(52) U.S. Cl. .................. 604/96.01; 604/103; 156/272.2; 156/272.6; 156/275.7; 156/294; 427/535; 427/536
(58) Field of Search .............................. 156/272.6, 273.3, 156/275.5, 275.7, 272.2, 293, 294; 427/536, 539, 535; 604/96, 103, 96.01; 204/164, 165, 168; 264/483

(56) References Cited

U.S. PATENT DOCUMENTS

| | | |
|---|---|---|
| 4,312,693 | * 1/1982 | Salensky et al. ................. 156/272.2 |
| 4,868,096 | 9/1989 | Muneo et al. ........................ 430/329 |
| 5,147,725 | 9/1992 | Pinchuk ............................. 428/425.5 |
| 5,277,753 | 1/1994 | Kelley et al. ......................... 156/643 |
| 5,364,662 | 11/1994 | Domenico et al. .................. 427/536 |
| 5,466,424 | * 11/1995 | Kusano et al. ....................... 427/536 |
| 5,662,960 | 9/1997 | Hostettler et al. .................... 427/2.3 |
| 5,683,757 | 11/1997 | Iskanderova et al. ............... 427/525 |
| 5,695,468 | * 12/1997 | Lafontaine et al. .................... 604/96 |
| 5,741,460 | 4/1998 | Jacob et al. ............................. 422/22 |
| 5,741,551 | 4/1998 | Guire et al. ........................ 427/407.1 |
| 5,759,173 | * 6/1998 | Preissman et al. ..................... 604/96 |
| 5,849,368 | 12/1998 | Hostettler et al. .................... 427/536 |

FOREIGN PATENT DOCUMENTS

| | | |
|---|---|---|
| 575 798 A1 | 12/1993 | (EP) . |
| 03041176 | 2/1991 | (JP) . |
| WO 86/01458 | 3/1986 | (WO) . |

* cited by examiner

*Primary Examiner*—Jeff H. Aftergut
*Assistant Examiner*—Michael A. Tolin
(74) *Attorney, Agent, or Firm*—Vidas, Arrett & Steinkraus

(57) ABSTRACT

A method of bonding polymeric materials, in particular, polymeric materials comprising silicone, is provided along with medical devices comprising materials bonded together by said method. More specifically, the method of the present invention involves surface treating the surface of a polymeric material, preferably a polymeric material comprising silicone, such that the character of the surface of the material changes in a manner such that bondability of the material is enhanced. The surface of the surface treated polymeric material is then brought into contact with the surface of a second polymeric material and optionally, an adhesive, under conditions effective to bond the surfaces together. The bond so formed is stronger than a corresponding bond between untreated polymeric materials.

16 Claims, 3 Drawing Sheets

METHOD OF BONDING POLYMERS AND MEDICAL DEVICES COMPRISING MATERIALS BONDED BY SAID METHOD

CROSS-REFERENCE TO RELATED APPLICATION

This application is a completion application of U.S. Provisional Application Ser. No. 60/078,839, filed Mar. 20, 1998 and claims priority therefrom. U.S. Provisional Application Ser. No. 60/078,839 is incorporated by reference herein.

FIELD OF THE INVENTION

The present invention relates to an improved method of bonding polymeric materials, in particular, polymeric materials comprising silicone, and further, to medical devices comprising materials bonded together by said method. More specifically, the present invention relates to a method of surface treating such materials so that the bondability of the materials is improved. The present invention further relates to medical devices formed at least in part from materials so treated and subsequently bonded together. Medical devices incorporating materials that are so treated exhibit increased bond strength and integrity.

BACKGROUND OF THE INVENTION

Many medical devices having a wide variety of clinical uses have been developed in recent years. For example, medical devices have been developed that can be used to replace indigenous mammalian organs that have become damaged and/or deteriorated, such as artificial heart valves or artificial joints; to help control or regulate defective organs, such as pacemakers; to replace damaged tissue, such as artificial skin grafts or breast implants; or to provide a less-invasive alternative to traditional treatment modalities, as is the case with intravascular therapeutic and diagnostic catheters. Such medical devices in the least often times represent a less traumatic treatment alternative, and often times, as is the case with artificial joints, represent the only viable treatment available.

However, such medical devices require exacting specifications in order to perform adequately under the rigorous conditions in which they are required to perform. Depending on the end use, such medical devices may be primarily comprised of polymeric materials that are non-thrombogenic, non-immunogenic, flexible, manipulatable, that exhibit both radial and longitudinal strength and/or, in certain applications, that are biodegradable. Inasmuch as there are very few single polymeric materials that provide this combination of characteristics, most medical devices are comprised of more than one polymeric material to provide the desired combination of physical properties. The use of multiple polymeric materials, in turn, requires that the polymeric materials be securely bonded together, as by the use of adhesive; direct bonding techniques, such as thermal bonding; and the like.

The bond sites of such medical devices, of course, are subject to the same exacting specifications of the overall device and thus, desirably exhibit a high degree of strength and integrity. For example, the bond sites must be able to withstand the handling and motion required to insert the device. Such bond sites also must be able to withstand the rigorous sterilization regimens, e.g., autoclave, ethylene oxide and gamma radiation sterilization regimens, to which medical devices are typically subjected. Additionally, the bond sites must be able to withstand any external pressure applied by the tissue into which it may be implanted or utilized. In medical devices such as intravascular catheters, the bond sites must be able to withstand the relatively high internal pressures, e.g., as high as 10 atmospheres to about 20 or more atmospheres, utilized to inflate the balloon portion of such catheters. Such high internal pressure not only affects the bond between the shaft portion of a catheter and the balloon, but also, since such high pressures can cause the shaft portion of the catheter to stretch and constrict, may affect other bonds present along the length of the catheter. As a result of these rigorous conditions, such bond sites must be strong enough to resist failure.

In the case of adhesive bonding, bond failure or weakness can result from a variety of circumstances. For example, the application of inadequate amounts of adhesive, as well as uneven application of adhesive, to a bond site can result in weakness or failure of the bond. Additionally, the use of an adhesive, as opposed to a direct bonding method, renders the bond site susceptible to failure as a result of the physical and mechanical properties of the adhesive itself. Finally, most adhesives rely on only the physical interaction, e.g., polar interactions or van der Waal's forces, between the adhesive and the surface to which the adhesive is applied for strength and integrity. Such a limited physical interaction provides inadequate bond strength for some applications.

Bond failure can also result from poor adhesion of the polymeric materials involved. For example, silicone rubber, while exhibiting many properties and characteristics otherwise desirable in the manufacture of medical devices, is difficult to adhere to any material, including itself. Thus, although silicone rubber has desirably low thrombogenicity, and is flexible and manipulatable, the incorporation of silicone and silicone-containing polymers into medical devices is problematic as such polymers generally do not adhere adequately with other materials typically used in medical device applications. Although functionalized monomers may be incorporated into a polymer to improve the adhesion of polymeric materials, such monomeric formulation modifications may fundamentally alter other desirable properties of the material.

Thus, it would be desirable to provide a method for improving the bondability of polymeric materials, particularly polymeric materials comprising silicone, that does not substantially alter the desirable properties of the polymeric material. It would further be desirable to provide medical devices incorporating such polymeric materials so that the bond sites of such devices would exhibit the desired integrity and strength.

SUMMARY OF THE INVENTION

The present invention relates to an improved method of bonding polymeric materials, in particular, polymeric materials comprising silicone, and further, to medical devices comprising polymeric materials bonded together by said method. More specifically, the method of the present invention involves surface treating a polymeric body, preferably a polymeric body comprising silicone, such that the character of the surface of the polymeric body changes in a manner such that bondability is enhanced. Furthermore, the method of the present invention enhances the bondability of the polymeric materials, while leaving the remaining, mechanical, physical and biological properties of the polymeric material substantially unchanged.

It has now been discovered that the bondability of a polymeric material may be enhanced by surface treating the polymeric material in a manner that changes the character of the surface of the polymeric material. More specifically, it has now been discovered that surface treating a polymeric material in a manner that results in the surface of the polymeric material becoming at least partially functionalized with chemically reactive moieties, e.g., hydroxyl groups, amide groups, amino groups, epoxy groups, carboxyl groups, ester groups, carbonyl groups, combinations thereof and the like, enhances the bondability of the polymeric material. This approach functionalizes the surface of the polymer, while leaving the bulk properties of the polymer substantially unchanged. By then choosing a compatible material or adhesive, i.e., a material or adhesive with functionality capable of chemically reacting with the functionality on the surface of the polymeric material, covalent bonding may take place between the surface treated polymeric material and the compatible material or adhesive. As a result, and in contrast to bonds between polymeric bodies and/or adhesives that are not so surface treated and that are largely based solely upon physical interactions between the bodies or the adhesive and the polymeric body, the bonds formed in the practice of the present invention provide the advantage of being based upon both physical and chemical interactions, and thus, are stronger bonds.

The method of the present invention has been found to work particularly well in enhancing the bondability of silicone, particularly medical grade silicone elastomers. Silicone is generally difficult to bond to other materials, including other silicone materials. However, surface treatment in accordance with the method of the present invention results in sufficient modification of the character of the surface of a silicone such that the bondability of silicone is enhanced. In the case of silicone, it is believed that surface treatment in accordance with the method of the present invention at least partially functionalizes the surface of the silicone body with hydroxyl groups, carboxyl groups, or both. By then choosing a material or an adhesive with functionality capable of reacting with the hydroxyl or carboxyl groups, the silicone body is then capable of forming covalent bonds with enhanced integrity and strength to such compatible materials and adhesives. For example, the silicone body is readily bondable with a compatible adhesive, e.g. a UV-curable adhesive with acrylic functionality to a wide variety of materials, including, for example, silicone, polyethylene, polypropylene, polyethylene terephthalate (PET), polyamide, polyacrylate, polyvinyl chloride, polycarbonate, urethane, fluorinated silicone and the like.

Thus, in one aspect, the present invention provides an improved method of bonding polymeric bodies, wherein at least one of the polymeric bodies comprises silicone. Specifically, the method comprises the steps of subjecting the surface of the polymeric body comprising silicone to a surface treatment under conditions effective to enhance the bondability of the surface of the polymeric body comprising silicone. Preferably, the surface treatment results in the surface of the polymeric body comprising silicone becoming at least partially functionalized with chemically reactive moieties. More preferably, the surface treatment results in the surface of the polymeric body comprising silicone becoming at least partially functionalized with hydroxyl functionality, carboxyl functionality, or a combination thereof. In one embodiment of the present invention, a compatible adhesive is then applied to at least a portion of the surface of the polymeric body comprising silicone, or alternatively to at least a portion of the surface of the polymeric body to which it is to be bonded, at least one of said surfaces and the surfaces of the two polymeric bodies are brought into contact under conditions effective to bond the surfaces. Preferably, the adhesive is a UV-curable adhesive with functionality capable of reacting with the hydroxyl functionality or carboxyl functionality on the surface of the polymeric body comprising silicone, e.g., the growing chain derived from acrylic functionality. In an additional embodiment, the surface of the polymeric body comprising silicone may simply be brought into contact with the surface of a second, compatible polymeric body under conditions effective to bond the surfaces without the use of an adhesive.

In addition to polymeric materials comprising silicone, the present invention is well suited to enhance the bondability of polymeric materials such as polyethylene terephthalates; polyether/polyester block copolymers; polyether/amide block copolymers; polyamides; polyimides; polyurethanes; hydrocarbon polymers such as polyethylene and propylene; synthetic hydrocarbon elastomers; natural rubber; fluorinated silicone polycarbonate; urethane; combinations of these and the like. Many of these polymeric materials find use in medical devices such as various types of catheters, and catheter devices for coronary angioplasty, including balloon catheters.

Thus, in another aspect, the present invention provides a medical device incorporating at least one material that has been treated by the method of the present invention. In one embodiment the present invention provides a medical device that comprises a first polymeric body comprising a first surface that has been subjected to a surface treatment such that the bondability of the first surface is enhanced relative to a similar, untreated first surface, a second polymeric body comprising a second surface comprising functionality compatible with the first surface, said second surface being in a confronting relationship to the first surface such that the first surface and second surface directly bond by virtue of the formation of covalent bonds. Preferably, the first surface is at least partially functionalized with chemically reactive moieties by virtue of the surface treatment. It is further preferred that the adhesive has functionality capable of reacting with the functionality on the first surface.

In a second embodiment, the present invention provides a medical device that comprises a first polymeric body comprising a first surface that has been subjected to a surface treatment such that the bondability of the first surface is enhanced relative to a similar, untreated first surface, a second polymeric body comprising a second surface, said second surface being in a confronting relationship to the first surface and a cured adhesive bonding said first surface to said second surface. Preferably, the first surface is at least partially functionalized with chemically reactive moieties by virtue of the surface treatment. It is further preferred that the adhesive has functionality capable of reacting with the functionality on the first surface. By treating the polymeric materials to be incorporated into the medical device in accordance with the method of the present invention, the materials maintain their desirable mechanical, physical and biological properties, while exhibiting increased bondability such that the resulting bond sites of the medical devices exhibit the desired integrity and strength.

BRIEF DESCRIPTION OF THE FIGURES

The above mentioned and other advantages of the present invention, and the manner of attaining them, will become more apparent and the invention itself will be better understood by reference to the following description of the embodiments of the invention taken in conjunction with the accompanying drawing, wherein.

DETAILED DESCRIPTION OF THE PRESENTLY PREFERRED EMBODIMENTS

Figure 1:
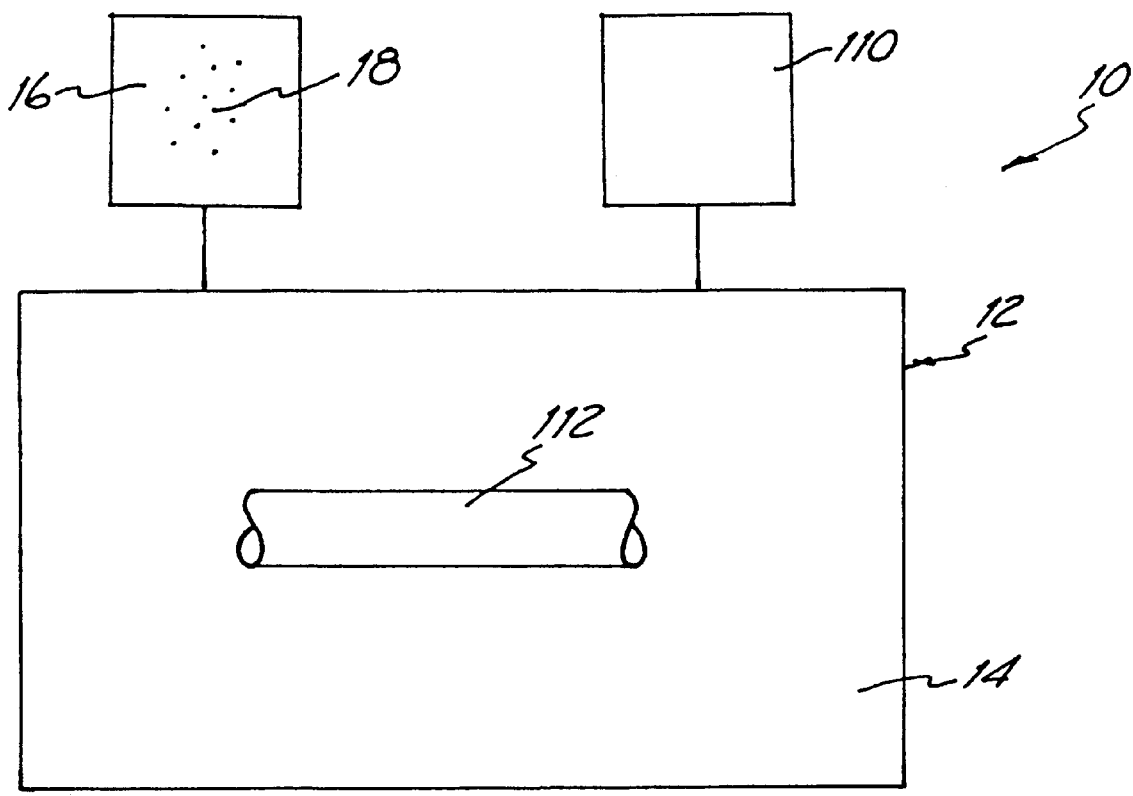
FIG. 1 shows a perspective view of an apparatus that may be used in the method of the present invention.

The embodiments of the invention described below are not intended to be exhaustive or to limit the invention to the precise forms disclosed in the following detailed description. Rather, the embodiments are chosen and described so that others skilled in the art may appreciate and understand the principles and practices of the present invention.

The present invention relates to an improved method of bonding polymeric materials, in particular, polymeric materials comprising silicone, and further, to medical devices comprising materials bonded together by said method. More specifically, the method of the present invention involves surface treating a polymeric body, preferably a polymeric body comprising silicone, such that the character of the surface of the polymeric body changes in a manner such that bondability is enhanced. Furthermore, the method of the present invention enhances the bondability of the polymeric materials to which the method is applied, while leaving the remaining, mechanical, physical and biological properties of the polymeric material substantially unchanged.

The method of the present invention comprises the steps of subjecting the surface of the polymeric material of which it is desired to enhance bondability to a surface treatment under conditions effective to change the character of the surface of the polymeric material. More specifically, the surface treatment in accordance with the method of the present invention results in the surface of the polymeric material becoming at least partially functionalized with chemically reactive moieties, e.g., hydroxyl groups, amide groups, amino groups, epoxy groups, carboxyl groups, ester groups, carbonyl groups, combinations of these and the like. Subsequent to the treatment, the polymeric material may be bonded to another material, e.g. by direct bonding to a compatible material or by applying a compatible adhesive to at least a portion of the surface of one of the materials. By then causing the surfaces to contact each other under conditions effective to bond the surfaces together, bonds much stronger than those achieved between similar, untreated materials are produced. As used herein, the phrase "compatible adhesive" is meant to indicate an adhesive comprising functionality capable of chemically interacting with the functionality on the surface of the polymeric material surface treated in accordance with the method of the present invention. Also, as used herein, the phrase "compatible material" is meant to indicate a material comprising functionality capable of chemically interacting with the functionality on the surface of the polymeric material treated in accordance with the method of the present invention.

While not wishing to be bound by any theory, it is believed that surface treatment enhances the bondability of the polymeric material by at least partially functionalizing the surface of the polymeric material with chemically reactive moieties such as hydroxyl groups, amide groups, amino groups, epoxy groups, carboxyl groups, ester groups, carbonyl groups, combinations thereof, and the like. By then choosing a compatible material or adhesive, i.e., a material or adhesive with functionality capable of reacting with the functionality on the surface of the surface treated polymeric material, covalent bonding may then take place between the surface treated polymeric material and the compatible material or adhesive. It is believed that the combination of this chemical interaction, i.e., the covalent bonds between the activated polymeric material and the adhesive, and the physical interaction, i.e., the "adhesion" between the polymeric material and the adhesive, makes the resulting bonds much stronger than those achievable when relying simply on the physical interaction between the adhesive and the polymeric material.

Any surface treatment capable of at least partially functionalizing the surface of a polymeric material with chemically reactive moieties is suitable for use in the method of the present invention. For example, suitable surface treatments include, but are not limited to, irradiating the surface of the polymeric material with an effective dosage of electromagnetic radiation, e.g., ultraviolet, infrared, or visible radiation; contacting the surface of the polymeric material with various oxidative reagents that may be gaseous, liquid, plasma, combinations of these and the like, such as oxygen, ozone, peroxides, oxygen-fluorine ($O_2/F_2$) mixtures, air/fluorine mixtures, fluorine mixtures, peroxygen acids and the like; plasma treatment, and the like. Preferably, the surface treatment utilized in the practice of the method of the present invention is an oxidative chemical treatment or an oxidative plasma treatment. More preferably, the surface treatment utilized in the practice of the method of the present invention is an oxidative plasma treatment The preferred oxidative plasma is a plasma formed from at least oxygen or a mixture of oxygen with air and/or one or more non-reducible gases, such as argon (Ar) and ammonia ($NH_3$).

Generally, a plasma is generated by creating an electrical discharge in a gaseous atmosphere maintained at a suitable pressure. Typically, plasma treatment systems comprise a chamber which is capable of being maintained at a desired pressure, e.g., sub-atmospheric or atmospheric pressure, within which the polymeric materials to be surface treated are placed and the appropriate electrical discharge is created. A number of gas plasma treatment systems suitable for use in the practice of the present invention are commercially available and such systems are generally known. One specific example of a preferred gas plasma treatment system is commercially available as a Plasma Science 350 from Himont/Plasma Science, Foster City, Calif. This system is equipped with an RF solid-state generator operating at 13.56 MHz and from 0 to 500 watts power output. It also includes a microprocessor controller and a complete vacuum pump package. The system further includes a treatment chamber having an unimpeded work volume of 42.5 cm by 34.3 cm by 17.5 cm.

A preferred plasma treatment apparatus for generating an oxidative plasma suitable for use as a surface treatment in the method of the present invention is shown in FIG. 1. Apparatus 10 includes gas plasma treatment system, represented schematically by reference numeral 12. System 12 is equipped with a treatment chamber 14 in which any of the polymeric materials, and/or portions of medical devices discussed below, are subjected to a gas plasma treatment in order to change the character of the surface of the polymeric material or portion. A gas source, schematically depicted by reference numeral 16, is operationally coupled to treatment chamber. 14 Gas source 16 provides a supply of oxidative gas 18 comprising oxygen and optionally one or more other treatment gases to treatment chamber 14. Preferably, oxidative gas 18 is oxygen, either pure or in air, or a mixture of oxygen with one or more non-reducible gases, such as argon (Ar) and ammonia ($NH_3$). More preferably, oxidative gas 18 comprises pure oxygen. In the embodiment shown in FIG. 1, oxidative gas 18 is converted into, and maintained as, a gas plasma within treatment chamber 14.

An energy source, schematically represented by reference numeral 110, is operationally coupled to treatment chamber 14 such that the energy source 110 is capable of supplying a sufficient amount of energy to ionize at least a portion of oxidative gas 18 to form a gas plasma. Three power sources have been widely used to supply such energy, including DC electrical energy, radio frequency (RF) energy, and microwave energy. Any of these three energy types, or the like, could be used as desired. However, an RF energy source generally has the greatest sensitivity and is most free from interference. An RF energy source is therefore preferred.

According to one procedure for using apparatus 10 to carry out the principles of the present invention, one or more polymeric material(s) 112 to be treated is/are placed into treatment chamber. 14 Chamber 14 is then evacuated to a desired base pressure of from about 10 millitorr (mTorr) to about 100 mTorr, preferably from about 30 mTorr to about 60 mTorr. Chamber 14 is then optionally cleaned by flowing a non-reactive gas, e.g., nitrogen, argon, helium, or mixtures thereof, through the chamber at rates of from about 10 standard mL per minute to about 750 standard mL per minute. Thereafter, oxidative gas 18 is admitted to the treatment chamber 14. A suitable supply rate of oxidative gas 18 would be about 10 standard mL per minute to 750 standard mL per minute, which is approximately equivalent to a pressure in the range from about 50 mTorr to about 500 mTorr. Suitable ionizing energy from energy source 110 is then applied to form the plasma. Using the Plasma Science 350 apparatus identified above, a power setting in the range of about 50 watts to 500 watts would be suitable, with a power setting in the range of from about 50 watts to about 400 watts being preferred. The polymeric material(s) 112 is/are then treated with the oxidative gas plasma for a time sufficient to enhance the bondability of the polymeric material(s). Generally, gas plasma treatment for a time period in the range from about 30 seconds to about 10 minutes would be suitable. After the plasma treatment, the polymeric material(s) 112 may be immediately removed from treatment chamber 14 as one option. Alternatively, polymeric material(s) 112 can be further conditioned in the atmosphere of oxidative gas 18 for an additional period of time, e.g., up to five minutes or more. The gas plasma treatment and/or conditioning steps may be repeated one or more times, if desired.

The above delineated operation parameters may be optimized depending upon what oxidative gas is utilized as oxidative gas 18. For example, if oxidative gas 18 is pure oxygen, it is preferred that apparatus 10 is operated at a base gas pressure of from about 0.01 Torr to about 0.09 Torr, preferably from about 0.05 Torr to about 0.09 Torr, and the flow rate of gas 18 is from about 10 standard mL per minute to about 100 standard mL per minute, preferably from about 80 standard mL per minute to about 100 standard mL per minute.

If oxidative gas 18 is a mixture of oxygen and ammonia, ($O_2/NH_3$), it is preferred that apparatus 10 is operated at a base gas pressure of from about 30 mTorr to about 90 mTorr. The $O_2:NH_3$ ratio is preferably maintained at from about 0.5:1 to about 5:1, more preferably at about 2:1. The ammonia gas flow rate is preferably from about 20 standard mL per minute to about 100 standard mL per minute, while the oxygen gas flow rate is preferably from about 80 standard mL per minute to about 100 standard mL per minute.

If oxidative gas 18 is a mixture of oxygen and argon, it is preferred that apparatus 10 is operated at a base gas pressure of from about 30 mTorr to about 100 mTorr. The $O_2:Ar$ ratio is preferably maintained at from about 0.5:1 to about 5:1, more preferably at about 2.5:1. The argon gas flow rate is preferably from about 40 standard mL per minute to about 100 standard mL per minute and the oxygen gas flow rate is preferably from about 80 standard mL per minute to about 100 standard mL per minute.

If oxidative gas 18 is a mixture of pure oxygen in air, it is preferred that apparatus 10 is operated at a base gas pressure of from about 30 mTorr to about 100 mTorr. The $O_2:Air$ ratio is preferably maintained at from about 0.5:1 to about 5:1, more preferably at about 1:1. The air gas flow rate is preferably from about 80 standard mL per minute to about 100 standard mL per minute and the oxygen gas flow rate is preferably from about 80 standard mL per minute to about 100 standard mL per minute.

For each oxidative gas 18, the plasma treatment and post oxidative gas treatment are desirably carried out long enough to achieve the desired degree of surface treatment, i.e., forming bondable functionality on the surface of the polymeric material. If both treatments are not carried out for a long enough period of time, or carried out too long, the bondability of the polymeric material may not be enhanced to the desired degree. As a guideline, the plasma treatment time is preferably from about 1 to about 5 minutes, more preferably from about 1 to about 3 minutes and the post oxidative gas treatment time is preferably from about 3 minutes to about 10 minutes, more preferably from about 3 minutes to about 5 minutes. Additionally, for all three exemplary oxidative gas 18 cases, apparatus 10 is preferably operated at an output power of from about 10 to about 500 Watts, preferably from about 50 to 400 Watts. It is further preferred that the temperature of chamber 14 varies from room temperature up to about 80° C.

Following such plasma treatment, the surface of polymeric material(s) 112 is at least partially functionalized with chemically reactive moieties, and thus the bondability of polymeric material(s) 112 is enhanced. The surface treated polymeric material may then be bonded to another compatible polymeric material, or, alternatively, be bonded to another polymeric material by application of the chosen compatible adhesive. If the surface treated polymeric material is to be directly bonded to another compatible polymeric material, the surface treated polymeric material is simply brought into contact with the surface of the compatible polymeric material under conditions sufficient to bond the surfaces of the two polymeric materials together. Optionally, such direct bonding may be catalyzed by application of energy from an appropriate energy source, e.g., electromagnetic radiation, electron beam irradiation, and the like, or by the utilization of appropriate chemical reagents, e.g., moisture, acids, bases, and the like.

If the surface treated polymeric material is to be bonded to another polymeric material by application of a compatible adhesive, the adhesive may be applied to the surface of the treated polymeric material, the surface of the material to which the treated polymeric material is to be bonded, or to both. If the adhesive is to be applied to the surface treated polymeric material, it is preferred that the adhesive be applied to the surface treated polymeric material within about 60 minutes, more preferably within about 30 minutes, of plasma treatment. After applying the adhesive, the surface treated polymeric material is brought into contact with the polymeric material to which it is to be bonded under conditions sufficient to bond the surfaces of the two polymeric materials together. If the chosen adhesive is radiation curable, the bond site is then desirably irradiated with an amount of curing energy sufficient to cure the adhesive.

Either one or both of the polymeric materials to be bonded may be surface treated in accordance with the method of the present invention. Specifically, if both of the polymeric materials to be bonded are known to be difficult to bond, both surfaces are advantageously surface treated in accordance with the method of the present invention. If, however, only one of the materials is known to be difficult to bond, surface treatment of only the material known to be difficult to bond will result in the enhanced bondability of the material and thus, enhanced bond strength between the two materials.

The method of the present invention may be applied to any polymeric material for which it is desired to enhance the bondability thereof, e.g., any material that is difficult to bond, and that comprises, or is capable of having imparted thereto, chemically reactive moieties. As used herein, the phrase "chemically reactive moieties" means moieties that are capable of undergoing chemical crosslinking reactions with corresponding compatible reactive groups of a compatible adhesive and/or a second polymeric body to be bonded. Such chemically reactive moieties include, but are not limited to, hydroxyl groups, amide groups, amino groups, epoxy groups, carboxyl groups, ester groups, carbonyl groups, and the like. Preferred chemically reactive moieties are those that are radiation crosslinkable so that bonding can occur quickly upon exposure to a suitable source of curing energy, e.g., heat; electromagnetic radiation, such as UV or infrared light; electron beam irradiation and the like. As used herein, the term "bondability" is meant to indicate the ability of a material to form chemical covalent bonds with another material or an adhesive. Thus, as used herein, the phrases "enhanced bondability" or "enhanced bond strength" are meant to indicate an improvement in the ability of a material to form a covalent bond, or an improved covalent bond strength, respectively, relative to the ability of a similar, untreated material to form a covalent bond, or to the covalent bond formed by a similar, untreated material, respectively.

Examples of polymeric materials that may benefit from surface treatment in accordance with the method of the present invention, include, but are not limited to, polyesters such as polyethylene terephthalate and the polyester elastomer commercially available under the trade designation "HYTREL" from E.I. DuPont deNeMours, Wilmington, Del.; polyether/polyester block copolymers; nylon polymers such as nylon-11 and nylon-12; polyether/amide block copolymers (such as that commercially available under the trade designation "PEBAX" from Atochem, Glen Rock, N.J.); polyamides; polyimides; polyurethanes; polyolefin polymers such as polyethylene (e.g., linear low density polyethylene (LLDPE), low-density polyethylene (LDPE), and high density polyethylene (HDPE) and polypropylene; natural rubbers; silicone rubber elastomers (such as that commercially available under the trade designation "40016 grade Silicone" from Applied Silicone Technology); polycarbonates; polyurethanes; polyacrylates; polyvinyl chloride; combinations of these, and the like.

In addition to polymeric constituents, polymeric bodies to be bonded may further comprise additional constituents such as antioxidants, ultraviolet and other light stabilizers, catalyst residues from manufacture, organic and inorganic fillers such as calcium carbonates, clays, barium sulfate used as the radioopaque filler for medical devices, carbon blacks and other pigments. If present, any such additional constituents may be used in accordance with conventional practices.

Preferably, the method of the present invention is used to enhance the bondability of a polymeric body comprising silicone to a second polymeric body comprising one or more polymers, e.g., silicone, polyester, polyether/polyester block copolymers, nylon polymers, polyether/amide block copolymers, polyamides, polyimides, polyurethanes, hydrocarbon polymers such as polyethylene and polypropylene, synthetic hydrocarbon elastomers, natural rubbers; silicone rubber elastomers; polycarbonates, polyurethanes; polyacrylates, polyvinyl chloride, combinations of these, and the like. More preferably, the method of the present invention is used to enhance the bondability of a polymeric body comprising silicone to a second polymeric body comprising a polyester elastomer or a polyether/amide block copolymer.

Inasmuch as many of the aforementioned polymeric materials find use in medical devices such as various types of catheters, and catheter devices for coronary angioplasty, including balloon catheters, the method of the present invention may be advantageously incorporated into the manufacture of various medical devices. By treating the polymeric materials to be incorporated into a medical device in accordance with the method of the present invention, the polymeric materials maintain their desirable properties, while exhibiting increased bondability such that the resulting bond sites of the medical devices exhibit the desired integrity and strength. Examples of such medical device applications include, but are not limited to, bonding a silicone catheter segment to a silicone or non-silicone catheter segment; bonding a silicone balloon to a silicone or non-silicone catheter shaft; bonding a silicon catheter tip to a silicone or non-silicone catheter segment (e.g., guiding angiographic and angioplasty catheters); bonding a silicone implant component to a silicone or non-silicone implant component; bonding a non-silicone catheter hub to a segment of silicone catheter tubing; and bonding a silicone film to a non-silicone or another silicone film.

Figure 2:
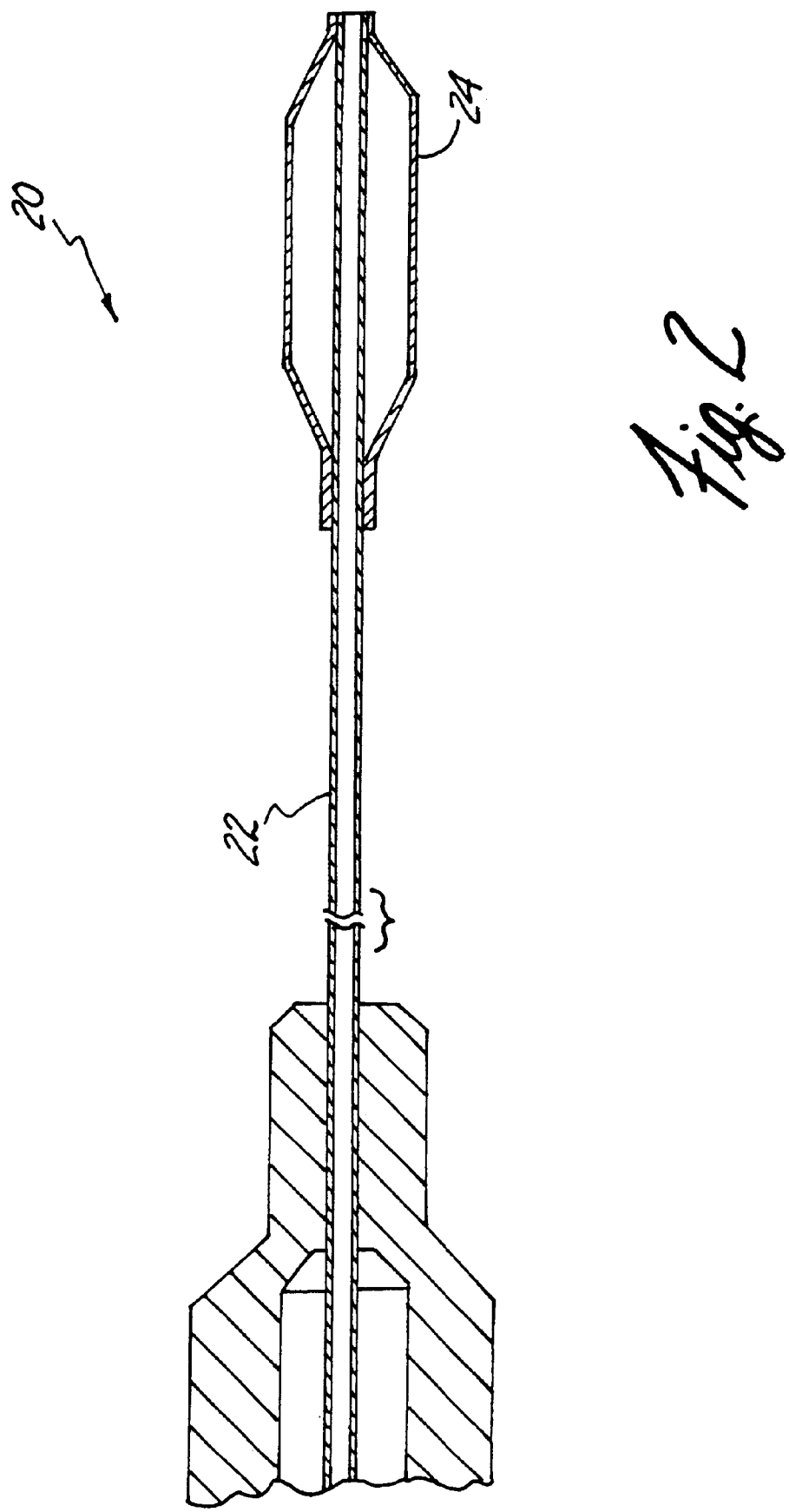
FIG. 2 shows a perspective view of a first representative medical device in accordance with the present invention.

One specific example of a representative medical device in accordance with the present invention is illustrated in FIG. 2. Specifically, FIG. 2 is a perspective view of a balloon catheter 20, e.g., as is used in coronary dilations. Balloon catheter 20 comprises shaft 22 and balloon 24. Shaft 22 may comprise any of the suitable materials listed hereinabove, or may be a multilayer tubing comprising combinations thereof. Balloon 24 preferably comprises a silicone rubber elastomer, and furthermore, preferably has a burst pressure of at least 10 atmospheres. As shown in the embodiment illustrated in FIG. 2, shaft 22 and balloon 24 are directly bonded, i.e., without the use of adhesive.

Figure 3:
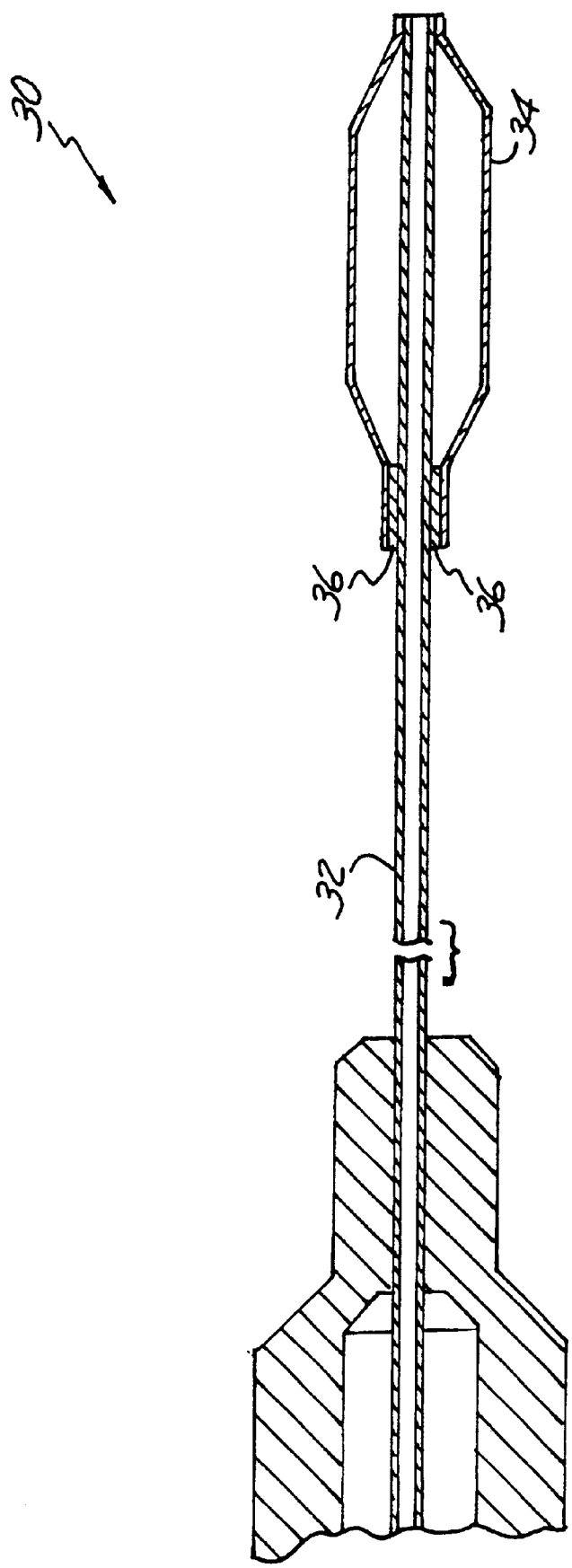
FIG. 3 shows a perspective view of a second representative medical device in accordance with the present invention.

In an additional embodiment of the medical device in accordance with the present invention, adhesive may be used to bond different components of the medical device. This embodiment of the invention is illustrated in FIG. 3. Specifically, FIG. 3 is a perspective view of a balloon catheter 30, comprising shaft 32 and balloon 34. Shaft 32 is bonded to balloon 34 with adhesive 36. Shaft 32 may comprise any of the suitable polymeric materials discussed hereinabove, or may be a multi-layer tubing comprising combinations of such polymeric materials. Balloon 34 preferably comprises a silicon rubber elastomer and furthermore, preferably has a burst pressure of at least 10 atm.

The surface treated polymeric material may be directly bonded to another compatible material, or alternatively, may be bonded to another material by the application of a compatible adhesive. If an adhesive bond is desired, any adhesive capable of chemically interacting with the chemically reactive moieties present on the surface of the surface treated polymeric material may be utilized in the practice of the method of the present invention. Preferably, the adhesive chosen will be capable of chemically interacting with the surface of the surface treated polymeric material, i.e., as by forming covalent bonds with the chemically reactive moieties on the surface of the polymeric material. For example, if the chemically reactive moieties are hydroxyl groups or carboxyl groups, suitable adhesives include UV curable adhesives (such as that commercially available under the trade designation "Dymax 189-MT" from Dymax, Torrington, Conn.), cyanoacrylate adhesives (such as that commercially available under the trade designation "Sicomet" from Henkels, Kanakee, Ill.), two part epoxy adhesives (such as that commercially available under the trade designation "Fusor" from Lord Company, Raleigh, N.C.). Urethane adhesives (such as that commercially available under the trade designation "Tyrite" from Lord Company, Raleigh, N.C.) and silicone adhesives (such as that commercially available under the trade designation "Med-1511" from NuSil Silicone Technology, Carpenteria, Calif.). Each of these adhesives is capable of forming covalent bonds with polymeric materials surface treated in accordance with the present invention by free-radical mechanisms, as is the case with UV adhesives, by ionic mechanisms, as is the case with cyanoacrylate adhesives, or by condensation mechanisms as is the case with epoxy, urethane and silicone adhesives.

Impurities, such as lubricants, antioxidants, plasticization agents, release agents, and the like, present on the surface of the polymeric materials to be surface treated and bonded in accordance with the method of the present invention can detract from the formation of the desired covalent bonds between the treated polymeric material and the chosen adhesive. Thus, the surface of the polymeric material may optionally be cleaned with polar or nonpolar solvents prior to surface treatment. Typical solvents which can be used for this purpose include alcohols such as methanol, ethanol, isopropanol, and the like; ketones such as acetone, methylethyl ketone, and the like; chlorinated hydrocarbons such as methylene chloride, 1,1,1-trichloroethane, and the like; hydrocarbons such as pentanes, n-hexane, petroleum ethers, other cleaning spirits, and the like; ethers such as diisopropyl ether, dioxane, tetrahydrofuran, and the like; and mixtures thereof It is also within the scope of the present invention to utilize aqueous solutions of nonionic anionic, and cationic surfactants as washing fluids, if desired, followed by rinsing with water or distilled water to remove any surface impurities that could otherwise potentially interfere with the surface treatment in accordance with the present invention.

The present invention will now be further described with reference to the following non-limiting examples.

EXAMPLE 1

Silicone (commercially available from NuSil Silicone Technology, Carpenteria, Calif.) was extruded to form tubing with an inner diameter (ID) of 0.060" and an outer diameter (OD) of 0.077". Bilumen polyether/amide block copolymer with a durometer of 25 D (commercially available under the trade designation "PEBAX", from Atochem, Glen Rock, N.J.) was extruded to form tubing with an OD of 0.051". Bilumen polyester elastomer with a durometer value of 45D (commercially available under the trade designation "Hytrel", from E.I. DuPont de NeMours, Inc, Wilmington, Del.) was extruded to form tubing with an OD of 0.053". The resultant extruded tubing was cut into 2.5 inch lengths and wiped clean with isopropyl alcohol. After drying at room temperature overnight, all the tubes were placed into the plasma chamber and treated with oxygen plasma. The oxygen plasma conditions and protocol are listed hereinbelow:

Step 1: $N_2$ purge
  time=2 minutes
  base pressure=50 mTorr
Step 2: Oxygen plasma treatment
  RF power=40%
  process time=3 minutes
  $O_2$ gas flow=100 $cm^3$/min
  base pressure=50 mTorr;
Step 3: Oxygen post-treatment
  RF power=0
  process time=5 minutes
  $O_2$ gas flow=100 $cm^3$/min
  base pressure=50 mTorr Within 30 minutes after the gas plasma treatment, UV-curable adhesive (commercially available under the trade designation "Dymax 189-mt" from Dymax, Torrington, Conn.) was applied on the distal 2–4 mm of the PEBAX and Hytrel tubes. The PEBAX and Hytrel tubes were then quickly inserted 2 cm into respective silicone tubes. The silicone and/or plastic tubes were rotated to ensure even distribution of the adhesive between the tubes. Each of the assembled tubes were then illuminated with a UV light (wavelength=365 nm) at a power output of 400 $mW/cm^2$ for 25 seconds at a distance of about 2 cm to cure the adhesive. Control samples were prepared in the same manner with the exception that the tubing was not surface treated prior to bonding.

The surface treated tube assemblies were then subjected to a variety of post-bonding treatments. Specifically, one group was held for three days at room temperature. An additional group was subjected to wet aging, i.e., held for 7 days at 55° C. and 80% relative humidity. Yet another group was dry aged; held for 7 days at 70° C. at less than 20% relative humidity. Finally, two groups were subject to sterilization treatments, specifically, one group was sterilized twice by ethylene oxide (ETO) sterilization while another group was sterilized once with gamma radiation at 25–38 Kgy.

Balloon burst tests were then performed to test the bonding strength of the samples. Specifically, the balloon burst tests were performed by connecting either the PEBAX or Hytrel end of the bonded tubing to a Touhy-Borst connector. The silicone end of the bonded tubing was folded and clamped. The measured start pressure inside each piece of bonded tubing was 5 psi. The pressure was then incremented successively by 5 psi and held 6 seconds at each pressure until the bond failed or the balloon burst. The results of the balloon burst experiments are shown below in Tables 1 and 2.

|  | Control | $O_2$ plasma 3d at RT | $O_2$ plasma wet aging | $O_2$ plasma dry aging | $O_2$ plasma 2× ETO | $O_2$ plasma Gamma |
|---|---|---|---|---|---|---|
| atm, burst/leak | 15, L | 25, L | 30, L | 30, B | 30, B | 25, L |
|  | 15, L | 25, L | 31, B | 30, B | 31, B | 30, L |
|  | 15, L | 25, L | 32, B | 30, B | 31, B | 29, L |
|  | 15, L | 20, L | 31, L | 33, B | 30, B | 31, B |
|  | 15, L | 28, L | 31. L | 34, B | 33, B | 29, L |

-continued

|  | Control | O$_2$ plasma 3d at RT | O$_2$ plasma wet aging | O$_2$ plasma dry aging | O$_2$ plasma 2× ETO | O$_2$ plasma Gamma |
|---|---|---|---|---|---|---|
|  | 15, L | 29, L | 31, B | 31, B | 30, B | 30, L |
|  | 15, L | 26, L | 31, B | 35, B | 30, B | 30, B |
|  | 15, L | 23, L | 31, B | 31, B | 30, B | 30, B |
|  | 15, L | 25, L | 30, B | 34, B | 32, B | 30, B |
|  | 15, L | 29, B | 31, B | 31. B | 30, B | 30, L |
| ave. pressure atm | 15 | 25.5 | 30.9 | 31.9 | 30.7 | 29.4 |

L = bond leak, B = balloon burst;
3d at RT = 3 days at room temperature; wet aging = 7 days at 55° C. and 80% relative humidity;
dry aging = 7 days at 70° C. at less than 20% relative humidity; 2× ETO = sterilized twice by ethylene oxide (ETO) sterilization; Gamma = sterilized once with gamma radiation at 25–38 Kgy.

|  | Control | O$_2$ plasma 3d at RT | O$_2$ plasma wet aging | O$_2$ plasma dry aging | O$_2$ plasma 2× ETO | O$_2$ plasma Gamma |
|---|---|---|---|---|---|---|
| atm, burst/leak | 15, L | 30, B | 33, B | 32, B | 32, B | 31, B |
|  | 15, L | 30, B | 31, B | 31, B | 32, B | 30, B |
|  | 15, L | 30, B | 32, B | 34, B | 32, B | 33, L |
|  | 14, L | 30, B | 34, B | 31, B | 31, B | 30, B |
|  | 15, L | 30, B | 32, B | 34, B | 31, B | 30, B |
|  | 13, L | 30, B | 28, L | 35, B | 31, B | 30, L |
|  | 15, L | 30, B | 30, L | 33, B | 31, B | 30, L |
|  | 15, L | 30, B | 31, L | 32, B | 31, B | 30, L |
|  | 15, L | 30, B | 31, L | 31, B | 31, B | 32, B |
|  | 15, L | 30, B | 32, B | 34, B | 31, B | 30, L |
| ave pressure atm | 14.7 | 30 | 31.4 | 32.7 | 31.3 | 30.6 |

L = bond leak, B = balloon burst;
3d at RT = 3 days at room temperature; wet aging = 7 days at 55° C. and 80% relative humidity;
dry aging = 7 days at 70° C. at less than 20% relative humidity; 2× ETO = sterilized twice by ethylene oxide (ETO) sterilization; Gamma = sterilized once with gamma radiation at 25–38 Kgy.

As is illustrated by the data in Tables 1 and 2, surface treatment in accordance with the method of the present invention significantly improved the bonding strength of silicone to the other polymers and resulted in balloon burst or leak at higher pressures than that of control samples in all instances.

What is claimed is:

1. A medical catheter, comprising:
   (a) a first polymeric body in the form of a first tube and comprising a first surface of silicone that has been subjected to an oxidative plasma surface treatment under conditions effective to functionalize at least a portion of the surface with chemically reactive moieties;
   (b) a second polymeric body in the form of a second tube and comprising a second surface, said first and second tubes being fitted one within the other such that the second surface is in a confronting relationship to the first surface; and
   (c) a cured compatible adhesive bonding said first surface to said second surface.

2. The medical device of claim 1, wherein the surface of the first polymeric body is subjected to the oxidative plasma treatment under conditions effective to provide said surface with hydroxyl functionality, carboxyl functionality, or combinations thereof.

3. The medical device of claim 2, wherein said adhesive, prior to being incorporated into said medical device, comprises functionality capable of forming covalent bonds with the functionality of the first surface, and wherein said functionality has reacted with the functionality of the first surface to covalently bond the adhesive to the first surface.

4. The medical device of claim 1, wherein the second polymeric body comprises a polyester elastomer.

5. The medical device of claim 1, wherein the second polymeric body comprises a polyether/amide block copolymer.

6. The medical device of claim 4, wherein the first polymeric body corresponds to a catheter balloon, and wherein the second polymeric body corresponds to at least one structure selected from the group consisting of a catheter hub, a catheter shaft, and a catheter tip.

7. A method of making a medical catheter, comprising the steps of:
   (a) subjecting a first silicone surface of a first tubular polymeric body to an oxidative plasma treatment under conditions effective to functionalize at least a portion of the first surface with chemically reactive moieties;
   (b) providing a second tubular polymeric body comprising a second surface, at least a first portion of the first tubular polymeric body and at least a second portion of the second polymeric body being fittable, one inside the other, with the respective first and second surfaces contacting each other;
   (c) applying a compatible adhesive to at least a portion of at least one of said surfaces; and
   (d) after applying the adhesive to at least a portion of at least one of said surfaces, fitting said portions of the first and second polymeric bodies together, thereby causing the surfaces to contact each other, under conditions effective to bond the surfaces together.

8. The method of claim 7, wherein the compatible adhesive is a radiation curable adhesive, and wherein said step (c) comprises treating the adhesive with curing energy under conditions effective to cure the adhesive.

9. The method of claim 7, further comprising the step of subjecting the second surface of the second polymeric body to a surface treatment under conditions effective to functionalize at least a portion of the second surface with chemically reactive moieties.

10. The method of claim 7, wherein the first polymeric body comprising silicone is in the form of a first tube, the second polymeric body is in the form of a second tube fitted inside the first tube, and wherein the adhesive is interposed between the tubes in order to bond the inner surface of the first polymeric body comprising silicone tube to the outer surface of the second polymeric body tube.

11. The method of claim 10, wherein the first polymeric body comprising silicone comprises a silicone rubber elastomer.

12. The method of claim 7, wherein the second polymeric body comprises a polyester elastomer.

13. The method of claim 7, wherein the second polymeric body comprises a polyether/amide block copolymer.

14. The method of claim 7, wherein the first polymeric body comprising silicone corresponds to a catheter balloon, and wherein the second polymeric body corresponds to at least one structure selected from the group consisting of a catheter hub, a catheter shaft, and a catheter tip.

15. The method of claim 7, wherein the surface of the first polymeric body comprising silicone is subjected to said oxidative plasma treatment under conditions effective to provide said surface with hydroxyl functionality, carboxyl functionality, or combinations thereof.

16. The method of claim 15, wherein the compatible adhesive comprises functionality capable of forming covalent bonds with said functionality.

* * * * *